United States Patent [19]

Skjold et al.

[11] Patent Number: 4,499,185

[45] Date of Patent: Feb. 12, 1985

[54] TEST FOR ESTERASE ACTIVITY IN A LIQUID SAMPLE

[75] Inventors: A. Christopher Skjold; Lonnie R. Stover; Robert W. Trimmer, all of Elkhart, Ind.

[73] Assignee: Miles Laboratories, Inc., Elkhart, Ind.

[21] Appl. No.: 378,895

[22] Filed: May 17, 1982

[51] Int. Cl.$^3$ .................. C12Q 1/44; C12Q 1/46; C12Q 1/42

[52] U.S. Cl. ..................... 435/19; 435/805; 435/20; 435/21

[58] Field of Search .............. 546/137; 435/19, 20, 435/21, 805; 436/16, 66

[56] References Cited

U.S. PATENT DOCUMENTS 4,299,917 11/1981 Berger et al. ................. 435/19

OTHER PUBLICATIONS

Pyttel et al., *J. Pharm. Sci.*, vol. 62, No. 4, pp. 684–685, 1973.

*Primary Examiner*—Blondel Hazel
*Attorney, Agent, or Firm*—Edward H. Gorman, Jr.

[57] ABSTRACT

A composition, test device and method for determining the presence of leukocytes, esterase and/or esterase activity in a test sample is disclosed. The composition comprises an ester which, when cleaved by esterolytic activity, produces a detectable response such as color formation. In addition the composition comprises the compound 3-quinuclidinol. The device is prepared by incorporating a carrier matrix, such as paper, with the composition. The method comprises contacting a test sample with the device and observing a detectable response.

15 Claims, No Drawings

TEST FOR ESTERASE ACTIVITY IN A LIQUID SAMPLE

BACKGROUND OF THE INVENTION

1. Field of the Invention

The present invention relates to the determination of the presence of leukocytes, or other esterase activity, in a test sample. Moreover, the invention relates to a semi-quantitative test which is rapid and which dispenses with the need for microscopic examination or wet chemistry laboratory procedures.

The presence of an abnormal level of leukocytes in a patient's urine is possibly indicative of such pathological conditions as kidney or urogenital tract infection or other dysfunction. Accordingly, accurate urinary leukocyte information can be an invaluable tool to the physician in diagnosis and treatment of such pathologies. Traditionally, the medical profession has relied on visual determination techniques to count leukocyte population in urine sediment or uncentrifuged urine, a process requiring expensive equipment such as a centrifuge and microscope, as well as a great deal of time on the part of the clinician. Moreover, the traditional techniques suffer from the inadequacy that only intact cells are determined. Leukocytes occurring in the urinary system are subject to conditions which can favor extensive cell lysis. For example, it is known that in urines of abnormally high pH, leukocyte half life can be as low as 60 minutes. Since lysed cells escape detection in visual examination techniques, erroneously low determinations and false negatives can result.

Of the two techniques of microscopic leukocyte analysis—urine sediment and non-centrifuged, homogenized urine—the former is clearly the most desirable. Although dependable results can inure to the latter, urine sediment observation is used in an overwhelming majority of instances. It requires that the urine sample be centrifuged and the sediment isolated and subjected to microscopic inspection. The analyst then counts the number of leukocytes appearing in the viewing field. However, this task is further complicated by the presence of other urinary components in the sediment such as epithelial cells and salt particles. The varying content of sediment constituents, coupled with other complicating factors including non-homogeneity of the sample and varying optical powers of microscope equipment, can lead to enormous errors in the ultimate determination.

It is thus apparent that a quick, facile method of leukocyte determination, one which would eliminate the need for time-consuming techniques, as well as cost-consuming equipment, and which would provide accurate results whether the cells were intact or had been lysed, would indeed advance the state of the art by a quantum jump. The present invention provides such an advance. It is based, not on the ability to see leukocytes, but on the enzymatic activity they exhibit, and therefore is not subject to the inaccuracies described above.

2. Description of the Prior Art

There exists in the prior art a body of references which disclose the use of certain esters which, when cleaved by enzymatic activity, result in the formation of color or other detectable species. Thus, British Patent No. 1,128,371 discloses the use of indoxyl and thioindoxyl esters as useful chromogens in detecting hydrolytic enzymes in body fluids. The enzymes cleave the ester to generate free indoxyl, which subsequently oxidizes to form the dimeric product indigo, a readily observable blue dye. Such activity is said to be due to, among other enzymes, cholinesterase. This patent also teaches that, in addition to the indoxyl portion of the ester substrate, the acid radical is chosen with particular reference to the enzyme to be detected. For example, it is stated that the acid radical can be acetate, laurate or stearate for detection of esterase or lipase. For detecting enzymes such as phosphatase or sulfatase the acyl radical can be inorganic. Thus, the British Patent can be held to teach the use of chromogenic esters as substrates for determining esterolytic enzymes, such esters comprising indoxyl or thioindoxyl as the alcoholic moiety of the ester, the acyl moiety being tailored to be conducive to the particular enzyme to be determined.

The effect of careful acyl radical selection is nowhere more clearly exemplified than in two references which demonstrate esterase specificity for esters in which the acyl radical comprises an N-protected amino acid or peptide. Thus Janoff, et al., *Proc. Soc. Exper. Biol. Med.* 136:1045–1049 (1971) teaches that alanine esters are specific substrates for esterase obtained from human leukocytes. Specifically this reference teaches that an extract of human leukocyte granules hydrolyzed n-acetyl-l-alanyl-l-alanyl-l-alanine methyl ester. Moreover, l-alanine-p-nitrophenol ester was similarly hydrolyzed to yield the yellow p-nitrophenol colorform.

Similarly, Sweetman et al., *Jour. Hist. Soc.*, 22:327–339 teaches the use of 1-naphthyl N-acetyl-DL-alanine and 1-naphthyl butyrate to demonstrate the presence of esterase, as well as 1-naphthyl N-acetyl-l-alanyl-l-alanyl-l-alanine.

U.S. Pat. No. 4,278,763, assigned to Boehringer Mannheim GmbH combines these teachings in arriving at the indoxyl or thioindoxyl esters of amino acids or peptides as still another example of a traditional colorogenic substrate for leukocytic esterase activity. Like the Janoff and Sweetman references, the Boehringer patent teaches the equivalence of proteases and esterase in their esterolytic penchants.

Other prior art teachings with respect to leukocyte determination include the peroxidative activity of granular leukocytes (U.S. Pat. No. 3,087,794). Such an approach, however cannot distinguish between leukocytes and hemoglobin, and one cannot tell whether a positive test is indicative of white or red blood cells.

Finally, there is available commercially a product known as "Cyturtest" which utilizes N-tosylalanine indoxyl ester referred to, supra. This product comprises a filter paper pad impregnated with the amino acid indoxyl ester. The pad is mounted on a plastic strip. When immersed in a leukocyte-containing urine sample, a color appears on the filter paper pad due to the formation of indigo. However, this test suffers from the drawback of having a considerably lengthy waiting period (about 15 minutes) before the test results can be assessed.

Thus, although the use of chromogenic esterase substrates is well-entrenched in the prior art, and despite the existance of esterase affinity towards indoxyl alaninate and peptidate, there exists no truly rapid test for leukocytes in urine. It is towards solving this problem that the present invention is directed.

Based on a concerted effort of research and development, it was discovered that a particularly facile test for the presence of leukocytes in urine could be had in a test time of only 3-4 minutes and less, thus overcoming a serious drawback of the prior art.

BRIEF SUMMARY OF THE INVENTION

Briefly stated, the present invention comprises a composition, test device and method for determining esterase activity in a test sample. The composition comprises (a) a chromogenic ester having the formula

R—O—R' in which R is a moiety which produces a detectable response when the ester is cleaved through an esterase or esterase-like esterolytic reaction, and in which R' is an amino acid or peptide moiety having a nitrogen protective group, and (b) 3-quinuclidinol. The device comprises a carrier matrix incorporated with the composition. The method comprises contacting the device with a liquid test sample and observing any detectable response in the carrier matrix.

DETAILED DESCRIPTION OF THE INVENTION

As used herein, the terms "esterase activity", "chromogenic ester", "detectable response", and "esterase or esterase-like reaction" and "esterolytic reaction" shall have the meaning defined as follows. "Esterase activity" shall mean that quality of a test sample whereby the sample behaves like the enzyme esterase. Accordingly, the presence of esterase activity in a test sample exhibits itself by being capable of cleaving a chromogenic ester substrate, defined below, and in such a manner as defined below.

"Chromogenic ester" shall mean an ester having the structure defined herein, in which one of the products of esterolytic cleavage, namely the alcoholic residue of such cleavage, is capable of producing a detectable response, either by itself or through further reaction.

By the term "detectable response" is meant a change in, or appearance of, a physical parameter which can be sensed by human or instrumental observation. Thus the detectable response can be the appearance of, or change in, visible color in the carrier matrix of the presently disclosed test device, or in a solution in which the composition is dissolved or suspended. The response can also be a change in the amount of light absorbed or reflected by the carrier matrix. For example the carrier matrix can be analyzed by use of a reflectometer or spectrophotometer. The reflected or absorbed light which is measured can be within a wide range of wavelengths, from infrared to ultraviolet. Alternatively, the detectable response can be in the form of the appearance of chemiluminescence. Depending on the selection of R in the chromogenic ester, i.e., the alcoholic moiety, it can be seen that a wide variety of detectable response is possible with the present invention, and the kind and degree of response is indeed broad in scope.

As used herein, the terms "esterase reaction", "esterase-like reaction" and "esterolytic reaction" shall apply to any reaction whereby the cleavage of a chromogenic ester into its alcoholic and acyl components is catalyzed, whether such catalysis is due to the presence of an esterase or whether it is attributable to some other sample component which exhibits esterase activity.

The chromogenic ester of the composition is characterized by two general criteria: an alcoholic moiety R which produces a detectable response when the ester is saponified or esterolytically cleaved, and an acyl moiety R which comprises an amino acid or peptide residue, wherein the amino group is substituted with a nitrogen protective group. Typical of R are such chromogens as indoxyl (3-hydroxyindole) and thioindoxyl and their derivatives, as well as p-nitrophenol, and p(β-nitrovinyl) phenol, Substituted and unsubstituted indoxyl and thioindoxyl moieties are described in British Pat. No. 1,128,371 and U.S. Pat. No. 4,278,763, both of which patents are incorporated herein by reference.

The acyl portion of the ester, i.e., the amino acid or peptide residue, is also intended as being broadly defined. Accordingly, the amino acid residue includes one of the α-amino acids in the L- or D-form. Especially preferred is L-alanine, but preferred embodiments also include glycine, valine, leucine, isoleucine, phenylalanine and tyrosine. Any free hydroxyl groups are preferably acylated.

If R' is to be a peptide, the present invention envisions those having about 1–5 amino acid constituents. Preferred are di- and tripeptides of the above-mentioned amino acids.

The N-protective groups which are conventionally employed in peptide chemistry, as well as others, are included herein by the term "nitrogen protective group". Included are such groups as acyl, oxycarbonyl, thiocarbonyl, sulphonyl, sulphenyl, vinyl, cyclohexenyl, phosphoryl or carbonyl.

Accordingly, the composition of the present invention comprises a chromogenic ester and 3-quinuclidinol. It has been found that inclusion of the latter compound dramatically decreases the reaction time of cleavage of a chromogenic ester by a sample having esterase activity. By inclusion of 3-quinuclidinol in the composition, read times are decreased several fold; from 15 minutes without the compound, to 2–3 minutes and less when it is present together with the chromogenic ester.

3-Quinuclidinol has the formal name of 1-azabicyclo [2.2.2] octan-3-ol, and has the structure

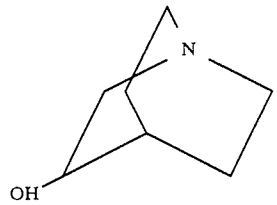

It exists in optically active isomeric forms, each of which has distinct physical properties. The dl-form can be crystalized from acetone or benzene to yield crystals melting at 225°–227° C., and which sublime at 120° C. and 20 mm Hg. The l-isomer forms prisms melting at 220°–222° C. The compound has been used by itself or as one of its derivatives as a hypotensive drug. See "Merck Index", Ninth Edition, page 1052, Entry No. 7905, Merck & Co., Inc., Rahway, N.J. (1976). It has also been reported as useful for cleaving β-keto esters. See "Aldrich Catalog Handbook", page 826, Aldrich Chemical Co., Milwaukee, WI (1981–1982).

Although the respective amounts of chromogenic ester and 3-quinuclidinol present in the composition is not deemed critical, it has been found desirable to that they be present at a molar ratio of ester to 3-quinuclidinol in the range of 1:5 to 100. It has been found especially useful to use a composition in which the molar ratio is 1:30 to 75.

In addition to the above ingredients, the composition may also contain an alcohol having 1–20 carbon atoms. Preferred is an alcohol having 8–12 carbon atoms. Illustrative of such alcohols which may be included in the composition, and which have been found especially preferred, are any of the isomers of decanol, especially n-decanol.

The test device of the present invention comprises a carrier matrix incorporated with the composition, thereby providing a tool for rapid, reliable estimations of the presence of leukocytes or other source of esterase activity in a test sample. The carrier matrix is usually, but not necessarily, a porous substance such as filter paper. Other art-recognized forms of carrier matrix materials are felt, porous ceramic strips, and woven or matted glass fibers (U.S. Pat. No. 3,846,247). Also suggested are the use of wood, cloth, sponge material and argillaceous substances (U.S. Pat. No. 3,552,928). All such carrier matrix materials are feasible for use in the present invention, as are others. It has been found that filter paper is especially suitable.

In a preferred embodiment, filter paper is wetted with a solution or suspension of solution of 3-quinuclidinol in aqueous buffer (pH about 8.5), or other suitable vehicle easily determinable by routine laboratory experiments, and then dried. The dried filter paper is subsequently incorporated with a solution of the chromogenic ester. Generally the ester solution is in an organic solvent, such as acetone. Other solvents which can be convenient to use include methanol, ethanol, N,N-dimethylformamide and dimethylsulfoxide. Following impregnation with the ester solution, the filter paper is dried to yield a test device sensitive to the presence of leukocytes or other source of esterase activity.

The dried, reagent-bearing carrier matrix can be mounted on a backing material if desired. Thus, a preferred embodiment of the test device, comprises a filter paper carrier matrix, incorporated with the composition as described supra, the matrix being affixed to one side to an elongated piece of transparent polystyrene film. The matrix is secured to one end of the film by any suitable means, such as double faced adhesive tape (Double Stick ® available from 3M Company), the other end of the polystyrene film serving as a handle. In use, such a device is held by the free end of the polystyrene film backing material and the matrix end is immersed into the test sample (e.g., urine) and quickly removed. Any color formation or other detectable response is observed after a predetermined time and compared with a reference standard corresponding to responses to known concentrations of leukocytes or other analyte having esterase activity. It has been found that an incubation time of about 1–3 minutes is sufficient to enable color development to occur in the reagent-containing filter paper.

EXAMPLES

The above-mentioned and other embodiments of the present invention can more easily be illustrated by reference to the following Examples. However, apart from their illustrative function, they are not intended, nor are they to be interpreted, as limiting in any way the scope of the invention.

EXAMPLE I

Control Test Device

An experiment was conducted to prepare a test device useful in determining the presence of leukocytes in a liquid test sample. Broadly, the device comprised a filter paper square (about 0.2 centimeters on a side) which had been impregnated with a chromogenic ester, indoxyl-N-tosylalaninate and n-decanol. A piece of filter paper was immersed successively in each of two dip solutions with drying following each immersion. The resultant dried reagent-containing paper was cut into 0.2 inch squares, one of which was attached to the end of an oblong polystyrene strip measuring about 4 inches by 0.2 inches. Adhesion between the paper and the plastic was achieved through the use of double-faced adhesive tape known as Double Stick, available from the 3M Company.

The first dip solution comprised a borate buffer solution to which was added an anionic detergent (Bio Terge AS-40) and potassium bromate. The borate buffer (pH=8.6) was prepared by adding 4.5 milliliters (ml) of a 0.2M boric acid solution to 5.5 ml of a 0.05M borax solution, all in distilled water. To this solution was added a sufficient volume of Bio-Terge AS-40(an anionic detergent available from Stepan Chemical Co.) to effect a 0.2 ml/deciliter (dl) solution. The resultant solution was made 10 mM (millimolar) in potassium bromate.

A piece of Eaton and Dikeman 205 filter paper was briefly immersed in the first dip solution and dried in an air oven at 100° C. for 20 minutes.

A second dip solution comprised an acetone solution of polyvinylpyrrolidone, n-decanol, quinine.HCl, and 3-(N-tosyl-L-alanyl-oxy) indole. The resultant concentrations of solutes were as follows:

1 ml/dl Polyvinylpyrrolidone in methanol (Luviskol available from GAF Corp.)
2 ml/dl n-Decanol
10 mM quinine hydrochloride
2 mM 3-(N-tosyl-L-alanyl-oxy)indole The dried filter paper from the first dip was immersed in the second dip and dried in an air oven at 60° C. for 5 minutes. A 0.2 inch square of dried paper was mounted on a polystyrene strip, as described, supra.

In order to test the efficacy of the test device in measuring the presence of leukocytes, a solution of contrived urine containing a known concentration of leukocytes was prepared and frozen subsequent to its use to assess the test strip. A portion of this contrived urine was defrosted and contained a leukocyte concentration of 3.3 leukocytes per microliter ($\mu l$). One of the devices was dipped into this test sample momentarily, removed, and allowed to incubate. After 14 minutes sufficient color had developed in the strip to enable a determination of a positive test.

EXAMPLE II

Effect of 3-Quinuclidinol

An experiment was conducted to test the effects of the compound 3-quinuclidinol on the performance of a strip similar to that prepared in Example I. Accordingly, the procedure of Example I was followed except that the first dip solution was made 50 mM in 3-quinuclidinol and 10 mM in potassium ferrocyanide (instead of bromate). Drying of the filter paper after the first immersion was at 80° C. for 25 minutes. Also, the second dip solution contained 0.2 ml/dl n-decanol, 1.5 ml/dl polyvinylpyrrolidone and 1.5 mM 3-(N-tosyl-L-alanyloxy)indole.

In order to assess the performance of the quinuclidinol-containing test device, the solution of contrived urine utilized in Example I was employed. Accordingly, the test device was dipped into the urine solution and allowed to incubate. After 4 minutes, sufficient color had developed in the reagent strip to indicate a positive for the presence of leukocytes in the contrived urine samples.

EXAMPLE III

A Preferred Embodiment

An experiment was conducted to further improve the results of Example II. Accordingly the procedure of Example I was followed, except as noted below, in preparing a test device.

The first dip solution comprised a pyrophosphate buffer at pH=8.6. This was prepared by making up a solution of 0.2M sodium pyrophosphate ($Na_4P_2O_7$) in distilled water, and adding slowly sufficient crystals of meta-phosphoric acid [$(HPO_3)_n$] until the resultant solution was at pH=8.6. To this solution was added a sufficient volume of Bio Terge AS-40 to effect a 0.2 ml/dl solution. Next, the solution was made 10 mM in potassium ferrocyanide, and 50 mM in 3-quinuclidinol.

A piece of Eaton and Dikeman filter paper was immersed in the first dip, removed and dried at 80° C. for 35 minutes.

A second dip solution was prepared in acetone. It contained 0.2 ml/dl n-decanol, 2.0 ml/dl polyvinylpyrrolidone in methanol (Luviskol), and 1 mM 3-(N-tosyl-L-alanyloxy) indole.

The dried filter paper from the first dip was immersed in the second dip, removed, and dried at 60° C. for 7 minutes. A 0.2 inch square of the resultant carrier matrix was mounted on a polystyrene strip as in Example I to form a test device.

The device was tested using three contrived urine samples, each having a specific gravity of 1.010 and being contrived to 0, 8.3 and 25 polymorphonuclear leukocytes per microliter (PMN/$\mu$l), respectively. These solutions were designated "negative", "trace" and "positive", respectively. The test devices were observed by six persons experienced in interpreting dip-and-read test devices. In order to assure objectivity in the observer, the contrived urine samples were not labeled. Each observer momentarily dipped a test device in a urine sample, removed it, and observed it after incubation periods of 1, 2 and 3 minutes.

A color chart was prepared for use in the study, i.e., for comparison with color developed in the test device, which had been prepared beforehand, corresponding to negative, trace (8.3 PMN/$\mu$l) and positive (25 PMN/$\mu$l), respectively. Thus, three devices prepared herein were dipped, one in each of three urine samples which were negative, trace and positive in leukocytes, allowed to incubate for 2 minutes, and the colors noted. Color blocks were then prepared corresponding to the color developed after 2 minutes in the test devices.

Each color block was assigned an arbitrary number: 10=negative, 20=trace and 30=positive. The six persons participating in the blind study were asked to read each strip at 1, 2 and 3 minute intervals following dipping and removing from a particular contrived urine sample. Each person then assigned a numerical value to color development for each time interval and for each urine sample. The results are as follows:

| Time (minutes) | Leukocyte Concentrations | | |
|---|---|---|---|
| | Negative (10) | Trace (20) | Positive (30) |
| 1 | 10.0 | 13.8 | 22.3 |
| 2 | 10.0 | 19.6 | 29.6 |
| 3 | 10.1 | 23.8 | 31.0 |

The data shows color differentiation between various leukocyte concentrations at 1 minute, with excellent differentiation at 2 minutes.

What is claimed is:

1. A composition for determining the presence of esterase activity in a liquid test sample said composition comprising
a chromogenic ester having the formula $$R-O-R'$$

in which R is a moiety which produces a detectable response when the ester is cleaved through an esterase or esterase-like esterolytic reaction, and in which R' is an amino acid or peptide moiety having a nitrogen protective group, and
3-quinuclidinol.

2. The composition of claim 1 in which R is indoxyl- or thioindoxyl.

3. The composition of claim 1 in which R is indoxyl.

4. The composition of claim 1 in which R' is an amino acid residue.

5. The composition of claim 1 in which R' is a peptide residue.

6. The composition of claim 1 in which R' is N-tosyl alaninate.

7. The composition of claim 1 in which the chromogenic ester is indoxyl-N-tosylalaninate.

8. The composition of any one of claims 1-7 in which the composition further comprises an alcohol having 1-20 carbon atoms.

9. The composition of claim 8 in which the alcohol is decanol.

10. A test device for determining the presence of esterase activity in a liquid test sample, said device comprising a carrier matrix incorporated with the composition of any one of claims 1-7.

11. A test device for determining the presence of esterase activity in a liquid test sample, said device comprising a carrier matrix incorporated with the composition of claim 8.

12. A test device for determining the presence of esterase activity in a liquid test sample, said device comprising a carrier matrix incorporated with the composition of claim 9.

13. A method for determining the presence of esterase activity in a liquid test sample, said method comprising the steps of contacting the test sample with the test device of claim 10 and observing a detectable response from the carrier matrix.

14. A method for determining the presence of esterase activity in a liquid test sample, said method comprising the steps of contacting the test sample with the test device of claim 11 and observing a detectable response from the carrier matrix.

15. A method for determining the presence of esterase activity in a liquid test sample, said method comprising the steps of contacting the test sample with the test device of claim 12 and observing a detectable response from the carrier matrix.

* * * * *